United States Patent
Douglas et al.

[11] Patent Number: 6,134,504
[45] Date of Patent: Oct. 17, 2000

[54] ANALYTE CONCENTRATION INFORMATION COLLECTION AND COMMUNICATION SYSTEM

[75] Inventors: Joel S. Douglas; Andrew M. Drexler, both of Los Altos Hills; Charles C. Raney, Sunnyvale; Edward C. Leung, Cupertino; Edison F. Yee, Los Altos, all of Calif.

[73] Assignee: Mercury Diagnostics, Incorporated, Scotts Valley, Calif.

[21] Appl. No.: 09/190,301

[22] Filed: Nov. 13, 1998

Related U.S. Application Data

[63] Continuation-in-part of application No. 08/963,674, Oct. 31, 1997.
[60] Provisional application No. 60/069,465, Dec. 15, 1997.

[51] Int. Cl.[7] ........................................ A61B 5/08
[52] U.S. Cl. ............................. 702/31; 128/904
[58] Field of Search ................................ 128/920, 904; 600/347; 702/22, 19; 340/870.01, 870.06, 875.06; 379/88.09, 88.14

[56] References Cited

U.S. PATENT DOCUMENTS

| | | | |
|---|---|---|---|
| 4,021,744 | 5/1977 | Montefusco | 329/105 |
| 4,531,527 | 7/1985 | Reinhold et al. | |
| 4,546,436 | 10/1985 | Schneider et al. | 364/415 |
| 4,731,726 | 3/1988 | Allen | |
| 4,803,625 | 2/1989 | Fu et al. | |
| 5,007,429 | 4/1991 | Treatch et al. | |
| 5,019,974 | 5/1991 | Beckers | |
| 5,025,374 | 6/1991 | Roizen et al. | 364/413.02 |
| 5,307,263 | 4/1994 | Brown | |
| 5,311,581 | 5/1994 | Merriam et al. | 379/107 |
| 5,357,427 | 10/1994 | Langen et al. | 600/300 |
| 5,516,700 | 5/1996 | Smith et al. | 436/164 |
| 5,549,117 | 8/1996 | Tacklind et al. | 128/716 |
| 5,771,891 | 6/1998 | Gozani | 128/635 |
| 5,820,570 | 10/1998 | Erickson et al. | 600/573 |
| 5,840,020 | 11/1998 | Heinomen et al. | 600/309 |
| 5,878,384 | 3/1999 | Johnson et al. | 702/187 |
| 5,899,855 | 5/1999 | Brown | 600/302 |

FOREIGN PATENT DOCUMENTS

| | | |
|---|---|---|
| 0601589A2 | 6/1994 | European Pat. Off. |
| 0684575A1 | 11/1995 | European Pat. Off. |
| WO94/14128 | 6/1994 | WIPO |

*Primary Examiner*—Timothy P. Callahan
*Assistant Examiner*—Linh Nguyen
*Attorney, Agent, or Firm*—Burns Doane Swecker & Mathis LLP

[57] ABSTRACT

A monitoring system which collects patient physiological date is designed specifically for communication with a communication module which facilitates data transfer from the monitoring system to a remote site. The communication module has data input mechanisms to facilitate setting parameters of the monitoring system and/or the communication module. The communication module is provided with a modem member which is used to communicate with the remote site and an optional data exchange module which is designed to communicate the same information with a local computer system. The remote site may be a bulletin board system or internet site where the monitoring information can be stored by the patient using the monitoring system by patient identification or name and include monitoring readings, time and date stamp, conditions such as meal times, exercise times and therapy amounts and their associated date and time.

65 Claims, 7 Drawing Sheets

ANALYTE CONCENTRATION INFORMATION COLLECTION AND COMMUNICATION SYSTEM

PRIORITY INFORMATION

This application claims the benefit of U.S. Provisional Application Ser. No. 60/069,465, filed Dec. 15, 1997, and is a C.I.P. of U.S. patent application Ser. No. 08/963,674, filed Oct. 31, 1997.

BACKGROUND OF THE INVENTION

1. Field of the Invention

The invention relates to the collection and communication of analyte concentration information, and more particularly, to a system for gathering and communicating such data for analysis and treatment.

2. Description of Related Art

Numerous simple test devices have been developed to test for presence and quantity of analytes in aqueous samples, particularly whole blood. The patent and technical literature of the last thirty years is replete with inventions which utilize a dry chemistry reagent system or electrochemical methods to test for analytes in bodily fluids. These systems have been designed so that they can capture various pieces of data such as time of day, date, calorie intake, exercise time and associated glucose readings.

A large government-sponsored study (the DCCT) demonstrated conclusively that careful control of blood glucose levels can significantly reduce the incidence of serious complications of diabetes such as vision loss and kidney malfunction. Most diabetics must test themselves periodically in order to make appropriate adjustments to their diet or medication. Thus, it is especially important for diabetics to have a simple and accurate means to capture their blood glucose readings and provide them to their health care provider for analysis of long-term control.

The technologies embodied in the products which have been developed to date all have certain limitations from the perspective of the end user and/or the manufacturer. The following review of prior art illustrates some of the many adaptations of the approaches which may be found in the patent literature. Numerous types of data collection systems have been utilized to capture reading from test devices for long-term analysis and therapy modulation. Many of these devices have been developed to interface with a local computer system and or upload the information to a disease management system.

Disease management system and the methods for data capture are taught in numerous patents and other prior art. U.S. Pat. No. 5,307,263 to Brown teaches a method which uses various monitors and a data management unit, a hand held unit and a modem to communicate with a clearing house and or user's computer.

U.S. Pat. No. 5,025,374 to Roizen et al. teaches a method of making and using an interactive medical test selector for use by a patient. It includes a memory device for storing the patient responses.

U.S. Pat. No. 4,731,726 to Allen III et al. teaches a method of monitoring a patient using a measuring device linked to a monitoring apparatus capable of receiving and storing data and using this information to generate insulin dosage recommendations.

U.S. Pat. No. 4,546,436 to Schneider et al. teaches the use of a device for continuous recording of physiological data. The system includes a data mapping and compression technique which permits long-term data acquisition.

U.S. Pat. No. 4,531,527 to Reinholdr et al. teaches a cardiac monitoring system which interfaces with an EKG and an office unit which can process the collected data.

U.S. Pat. No. 4,803,625 to Fu et al. describes a personal health monitor which includes sensors and is coupled to a central unit via modems and a computer which is programmed to prompt a patient to take prescribed medication at specific times.

U.S. Pat. No. 5,007,429 to Treatch et al. describes a user interface for direct programming of operating parameters for patient testing of blood pressure and downloading the data to an office control unit.

U.S. Pat. No. 5,019,974 to Beckers describes a diabetes management system and apparatus for efficient medical control for diabetes comprising a recorder, interface module, and master computer which can develop programs of therapy which can be downloaded to the recorder to remind the patient of pending therapy actions.

SUMMARY OF THE INVENTION

The invention overcomes the shortcomings of the prior art by providing a monitoring system designed specifically for communication with a communication module which facilitates data transfer with a remote site. The communication module has data input mechanisms to facilitate setting parameters of the monitoring system. The communication module more specifically has a modem member which is used to communicate with the remote site and an optional data exchange module which is designed to communicate the same information with a local computer system. The remote site is preferably a bulletin board system or internet site where the monitoring information can be stored by the patient using the monitoring system by patient identification or name and include monitoring readings, time and date stamp, conditions such as meal times, exercise times and therapy amounts and their associated date and time.

The communication module can comprise the data transfer mechanisms described above and may also contain data entry devices for inputting information such as time and date which can then be downloaded to the monitoring system to reset these parameters. Additional features which can be included in the communication module include function and data input keys to input other disease state information and a display for viewing this manually entered data.

The system may also be adapted to download from the remote site or a local computer time and date information to permit the communication module to automatically set or change the time and date system in the communication module and/or the monitoring device. One advantage of the invention is the simplification of the data capture method and the presence of a data collection system which is accessible by all patients to capture their data and permit it to be reviewed by their specific health care professional. An additional benefit is the simplification of the disease management by elimination of the need for noncomputer-trained patients to manually record all their data. Another benefit of the system is the reduction in size and the convenience provided by elimination of the data communication functions and elimination or reduction in size of the user interface means required to scroll through data stored in the monitor, set time and date, and communicate with current data management systems.

Rather than using a conventional modem, in one aspect of the invention information is communicated to and from the remote sites using a simplified information transfer format, with the transmitted data being encoded using an abridged character set which may be supplemented with a pneumonic transfer code for increased transmission speed. The abridged character set reduces the cost of the system by requiring encoding and transmitting equipment which is less costly than typical modems, and by reducing the transmission time length.

BRIEF DESCRIPTION OF THE DRAWINGS

Many objects and advantages of the present invention will be apparent to those skilled in the art with a reading of this specification in conjunction with the attached drawings, wherein like reference numerals are applied to like elements and wherein.

DESCRIPTION OF THE INVENTION

This invention provides physiological information collection and communication for patient disease management through the utilization of a system comprising a monitoring instrument, communication device and remote data collection site, thereby providing many benefits to patients controlling their disease state with intensive therapy. One such a task is the tight control of diabetes where the patient derives substantial benefit therefrom. Of course it is contemplated that the device can be used for testing for any analyte and it is not intended that the scope be limited to patient physiological data.

Figure 2:
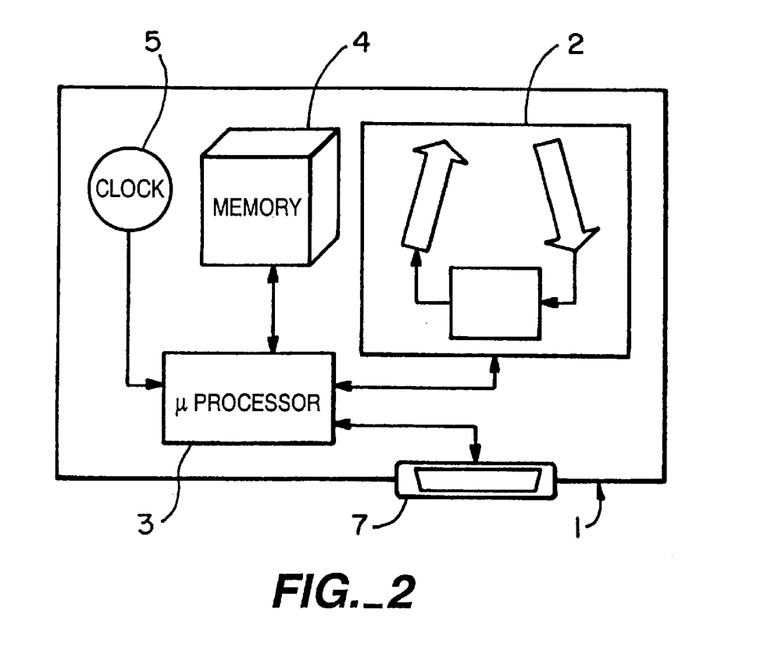
FIG. 2 is a schematic representation of a monitoring instrument in accordance with the invention.
Figure 3:
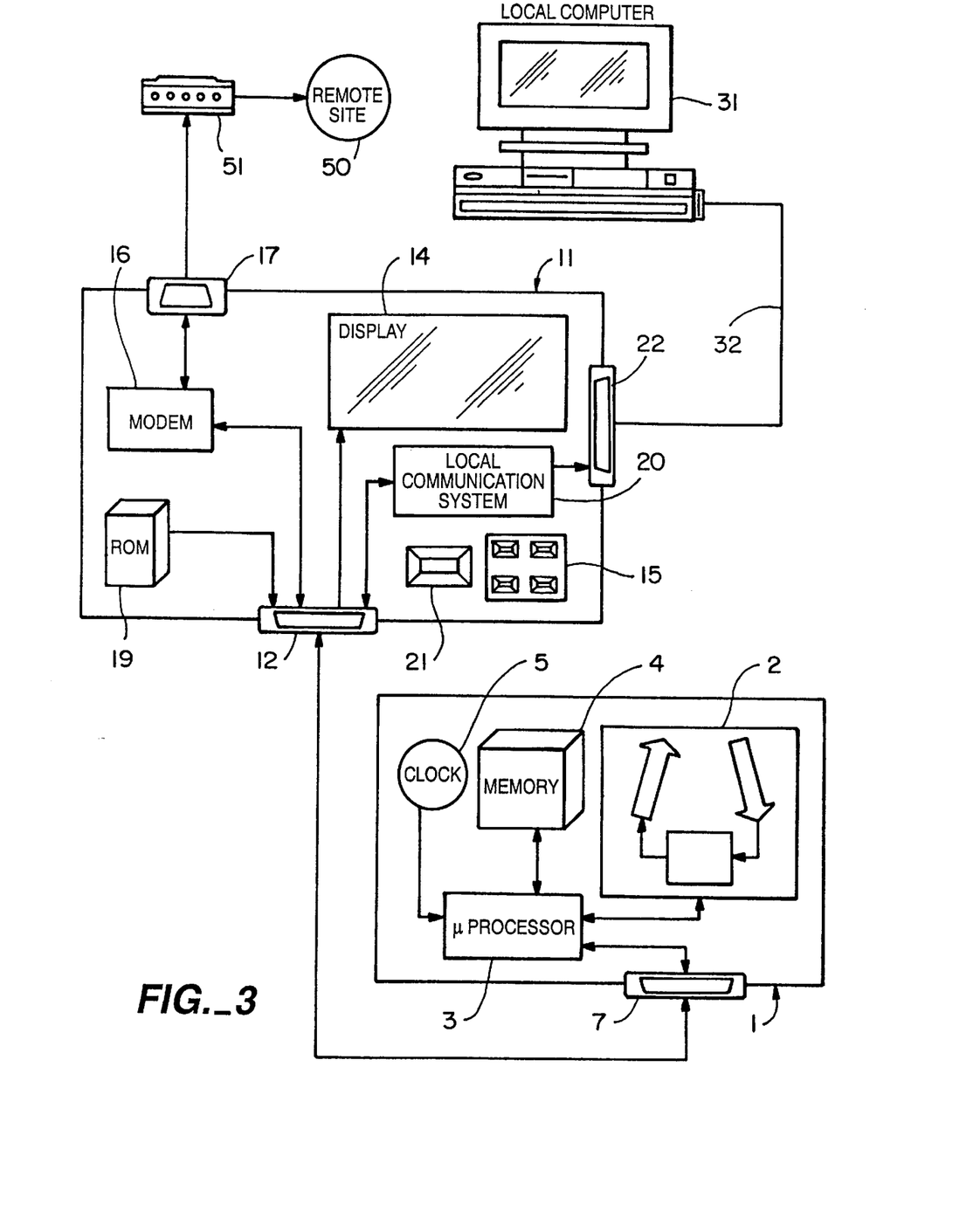
FIG. 3 is a schematic representation of the communication module, the monitoring instrument and the remote locations in accordance with an embodiment of the invention.

As seen in FIG. 3, an arrangement in accordance with the invention comprises a monitoring instrument 1 (FIG. 2) which can be used to gather physiological information during a collection mode. This physiological information may be the presence or concentration of an analyte of the patient, such as blood glucose level for diabetes control and treatment, or an analyte of urine or of intersticial fluid. The gathered information may be converted into information data and stored for uploading, via a communication module 11 during an interface mode, at a later time. The monitoring instrument 1 comprises a detection/analysis system 2 which is used to gather patient physiological data, such as blood glucose level, in any manner familiar to those skilled in the art, and may include optical testing of a sample on a sample strip impregnated with a suitable reagent. In such an optical arrangement, the analyte in the sample reacts with the reagent, with the reaction producing a physically detectable change which may entail an increase or decrease of a certain color component readily detectable via, for instance, electro-optical observation and measurement. LEDs and photodetectors may be used for this purpose in a well known manner. Alternatively, conductive probes may be used to measure the changed electrical conductivity between points on the sample strip due to the progression of the reaction of the analyte with the reagent.

As shown in FIG. 2, the monitoring instrument 1 is also equipped with a memory module 4 which is used for storing various information, including the gathered physiological information and instructions for proper operation of the monitoring instrument 1. Control of the monitoring instrument 1 is effected using a microprocessor 3 operating in conduction with a system clock 5. A rechargable battery pack or other power source (not shown) may be provided to furnish the necessary power for operation.

Figure 6:
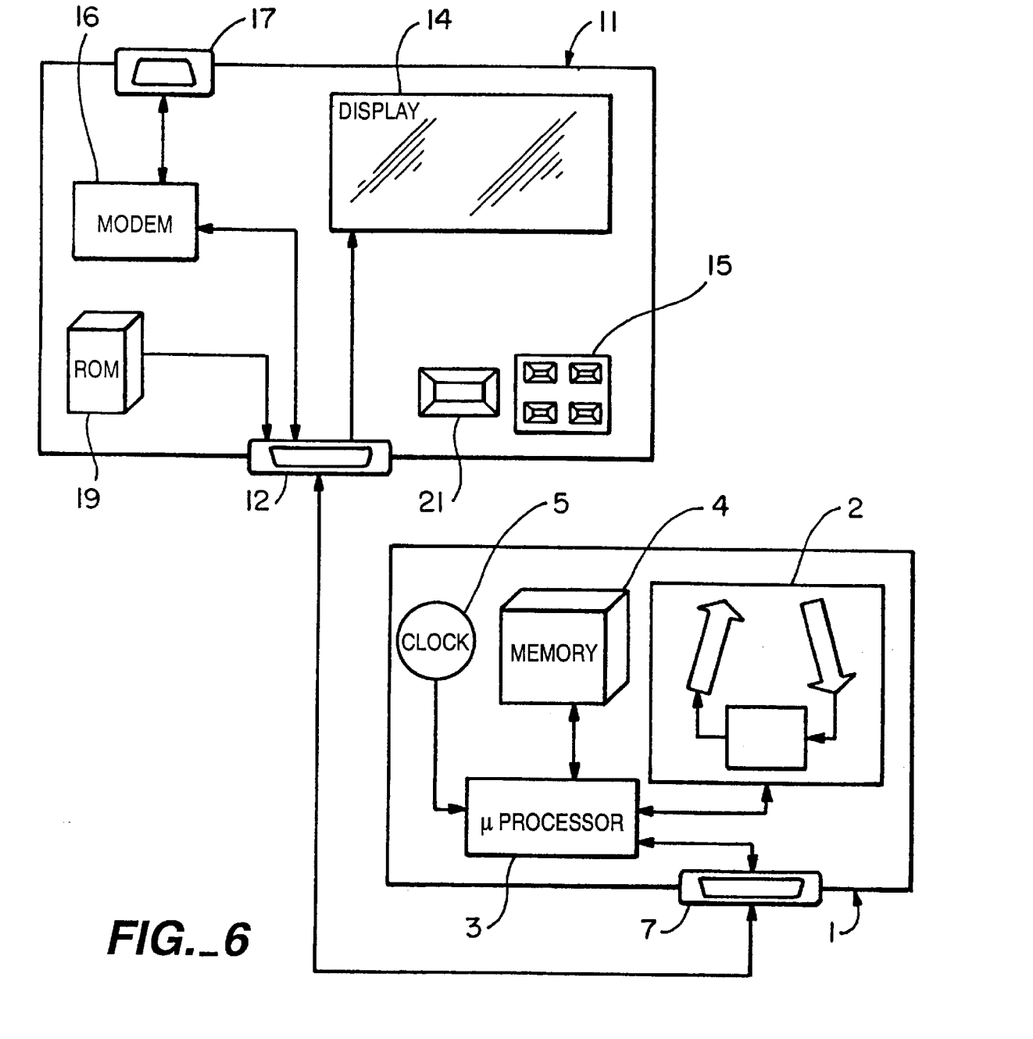
FIG. 6 is a schematic representation of a communication module in connection with a monitoring instrument in accordance with the invention.

In practice the patient may use the monitoring instrument 1 for some number of times to effect the collection of the physiological information. Subsequently, the patient connects the monitoring instrument 1 with a communication module 11 (FIG. 1) which establishes communication with the monitoring instrument 1 and reads the data stored in the memory of the monitoring instrument 1 during an interface mode. The interface mode is illustrated schematically in FIG. 6. The connection between the monitoring instrument 1 and the communication module 11 can be via cable, using e.g., a connection port 12, or it may be more direct, through physical mating of the two devices such that associated leads or pins contact each other to establish an electrical connection. Other communication schemes between the two devices are also contemplated and may include optical or ultrasonic ("remote control") type connections. The interface mode may also entail a charging session concurrent with the other interface activities, such as the memory download, and would comprise the use of a battery charging system (not shown) provided in or with the communication module 11 which engages the battery pack of the monitoring instrument 1 for recharging thereof.

Figure 1:
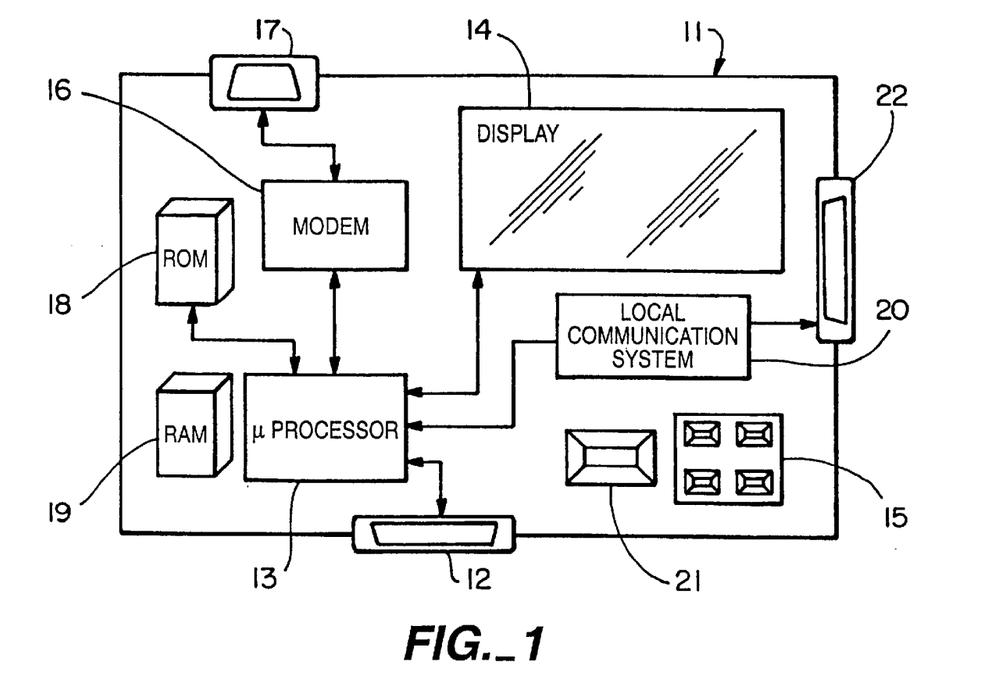
FIG. 1 is a schematic illustration of the communication module in accordance with an embodiment of the invention.
Figure 4:
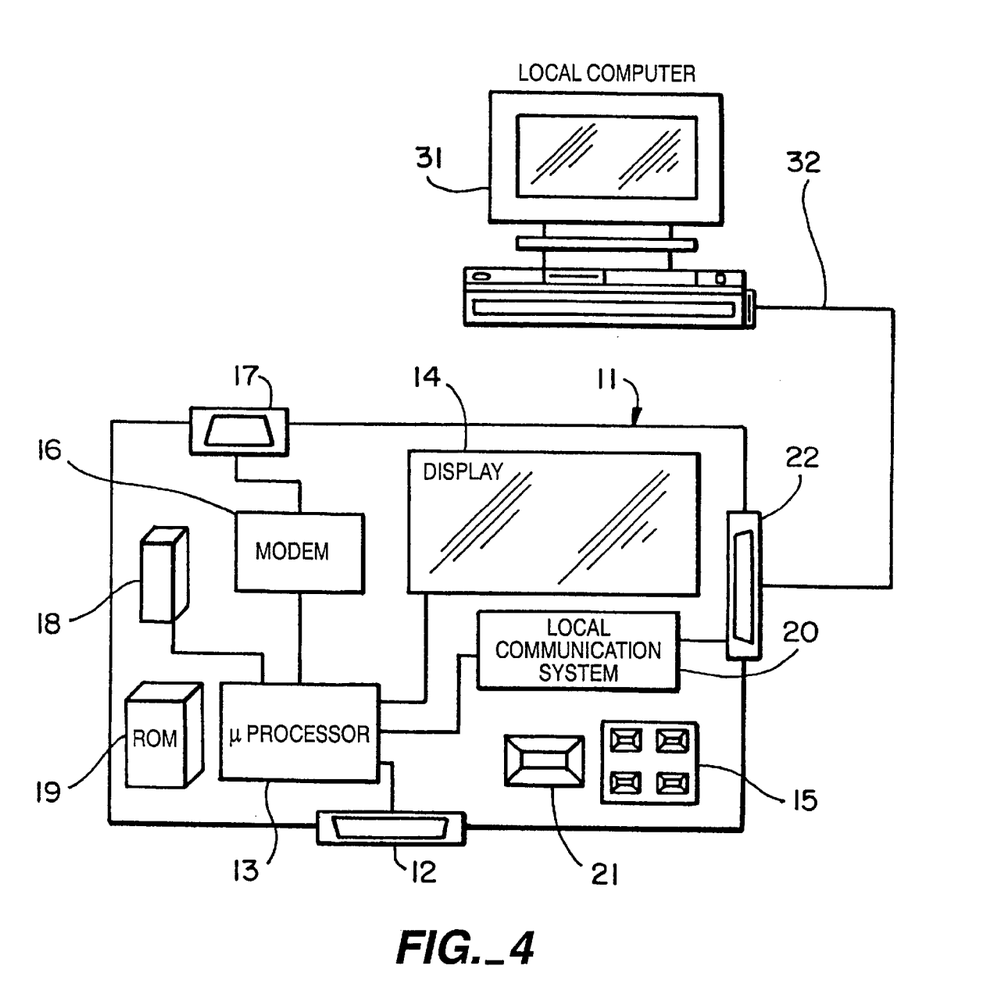
FIG. 4 is a schematic representation of the communication module in communication with a local computer in accordance with the invention.

As shown in FIGS. 1 and 4, the communication module 11 comprises a microprocessor 13 which controls the operation of the various components, including a display 14, data entry means 15, transfer mode selection device 21, random access memory 18, read only memory 18, serial or parallel local computer system communication system 20 and modem system 16. The communication module 11 is provided with a telephone system connection means 17 and local system connection means 22 which effect the linking functions for connection and communication with remote locations such as sites 50 (FIG. 7) which may be an internet location or an electronic bulletin board, or a local computer 31 connected via, e.g., a cable link 32 (FIG. 4).

Figure 7:
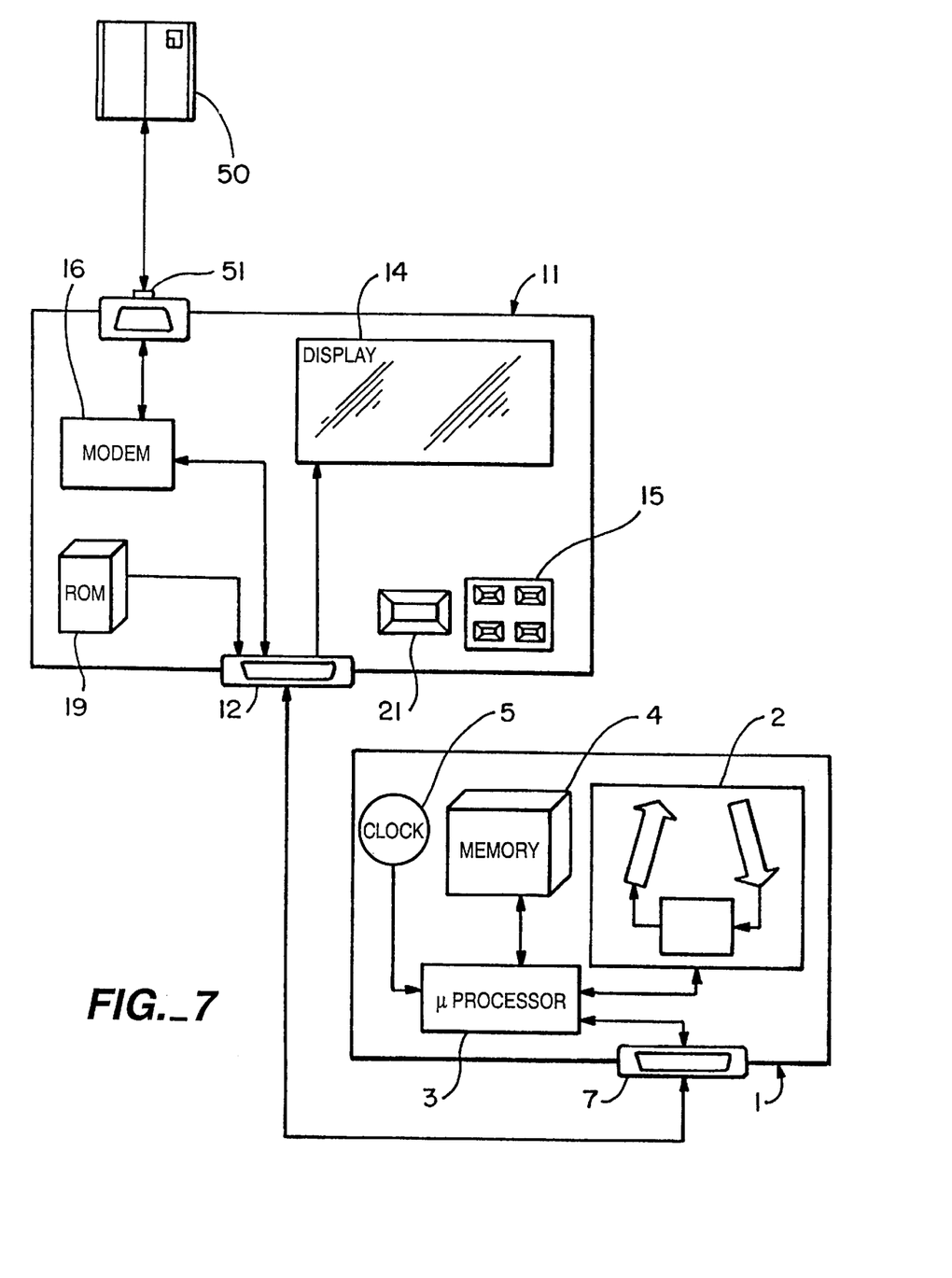
FIG. 7 is a schematic representation of the communication module in connection with the monitoring instrument and a remote location in accordance with the invention.

The patient can use display 14 of the communication module 11 to review the data, or the communication module can be permitted to automatically contact the remote site 50 or local computer 31 and transfer the data to a data storage system (not shown) provided at the remote location. Such automatic transfer would require little or no involvement by the patient—the communication module 11 senses the presence or connection of the monitoring instrument 1 thereto and automatically commences information transfer to the remote site 50 and/or local computer 31. The information exchange between the communication module 11 and the remote locations may be bidirectional, such that the data storage system at the remote location is capable of transferring correct time and date and other information to the communication module 11, which can use it to reset its clock and/or the clock in the monitoring device 1.

Two types of communication are selectable by the patient through the data entry means 15, which may be a control pad or key pad or other input mechanism. The patient, after connecting the monitoring instrument 1 with the communication module 11, can select either a local transfer (to, e.g., the local computer 31 as shown in FIG. 4) or a remote transfer of data to a data storage system disposed at the remote site 50 such as the internet site or electronic bulletin board (FIG. 7). As discussed above, it is contemplated that the transfer itself can be automatically activated upon completion of the connection process of the monitoring instrument 1 and the communication module 11, e.g., in a situation where these two components matingly engage each other, sensors can be provided which detect the successful fitting of the components to thereby commence the transfer process. It is also contemplated that the processor in the monitoring instrument 1 can be used instead of a processor in the communication module 11 to control the communication module 11 and/or to control and transfer data. Similarly, the communication module 11 need not be equipped with both a modem module and a data transfer module—one or the other could suffice to serve both functions. The telephone system connection means 17 can be replaced with an alternate internet connection to facilitate communication with the remote site 50.

Figure 5:
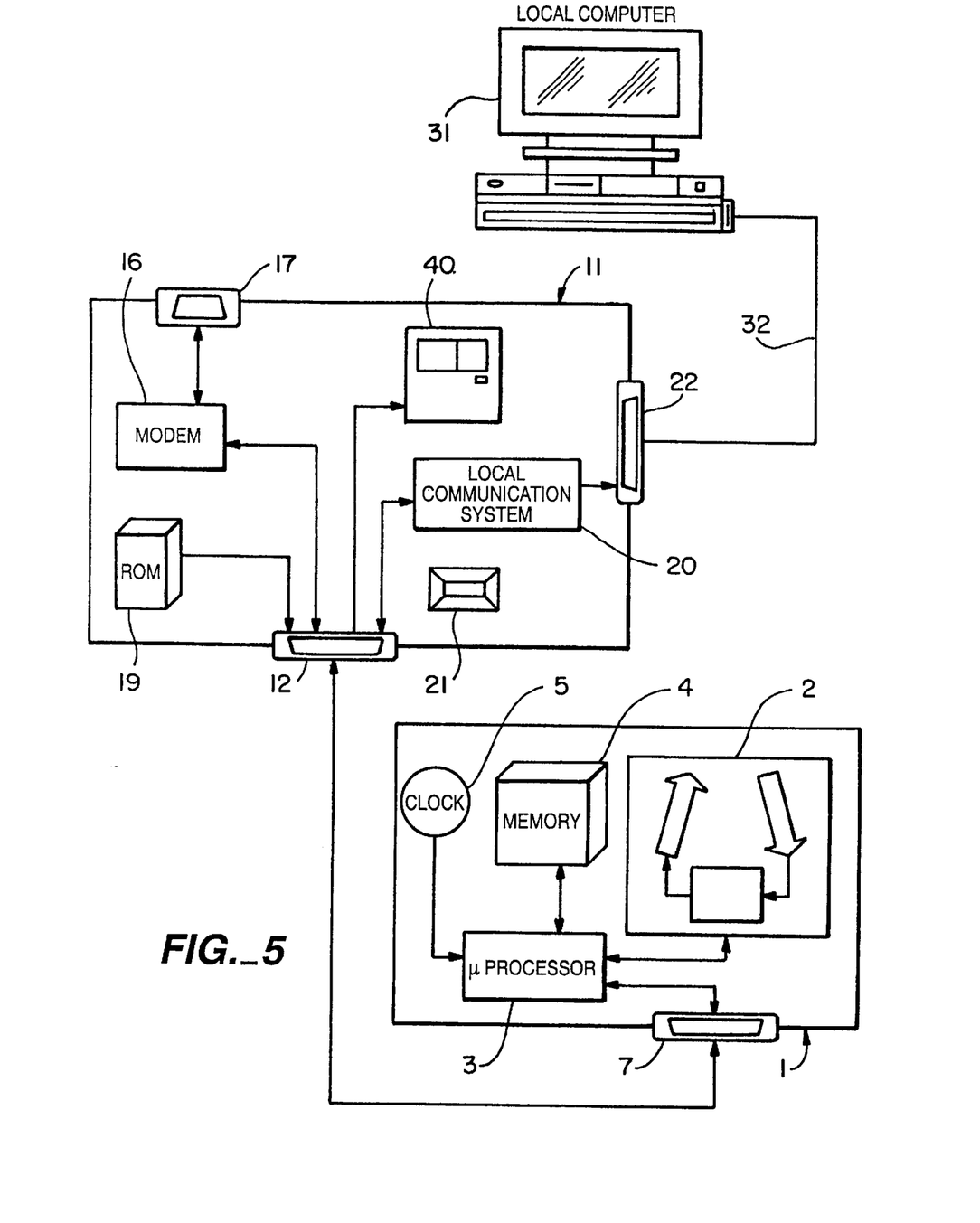
FIG. 5 is a schematic representation of a system in accordance with the invention in which a voice recognition system is employed.

The system of the invention can also be configured with the appropriate user interface for user supplied information and/or review of the captured data. Such a user interface can be a keypad (not shown) with a display device. The system can also be configured to compensate for various handicaps such as vision or hearing impairments of the user. A vision-impaired system could have an attachment means to permit the use of a larger display or voice recognition and response system. Alternately, it may have the voice recognition system incorporated into the communication module, enabling the communication module to respond the user's voice commands. Such devices have been developed for various computer systems such as IBM compatible personal computers. FIG. 5 shows an embodiment in accordance with the invention in which a voice recognition system 40 supplements or replaces the communication module's display 14 and/or data entry system 15.

In operation, the patient uses the monitoring instrument 1 to determine his or her glucose level and the information, which is used to generate information data, is stored in the memory module 4 of the monitoring instrument along with the time and data information. Alternately, the patient may enter his or her exercise or insulin therapy and that action is time and date stamped and stored in the memory module 4, which may comprise a conventional RAM (random access memory) device. At a convenient time and possibly after a number of such events have been recorded by the monitoring instruments, the patient uses the communication port 12 and places the monitoring instrument 1 in communication with the communication module 11. Then, in a transmission mode, the patient selects the data storage system to where the data is to be transferred and initiates the data transfer, or the communication module 11 automatically initiates the transfer by sensing the monitoring instrument 1 as discussed above. The communication module 11 may be equipped to provide an indication that the transfer is in progress and initiates communication with the selected data storage system. The information data is read or transferred from the monitoring instrument 1 or stored in the communication module 11 random access memory 18 for transfer to the data storage system at a later time. If the data storage system is a remote site (50) such as bulletin board or internet site, the modem system 16 is initialized and communication protocol initiated between the communication module 11 and the compatible modem system (not shown) on the data storage system. If the system is to communicate with a local system, such as computer 31, the parallel or serial communication protocol is initiated with the local computer system 31. The information data is then transferred and the data storage system can transfer the correct time and date information back to the communication module 11 where it is used to update the communication module clock and/or the monitoring instrument clock 5. After the transfer is complete, the communication module 11 releases a transfer-in-progress indicator (not shown) and terminates the communication protocol with the data storage system. The monitoring system may be left in the communication module until needed by the patient while an optional charging circuit in the communication module recharges the batteries of the monitoring system prior to the next monitoring event.

Figure 8:
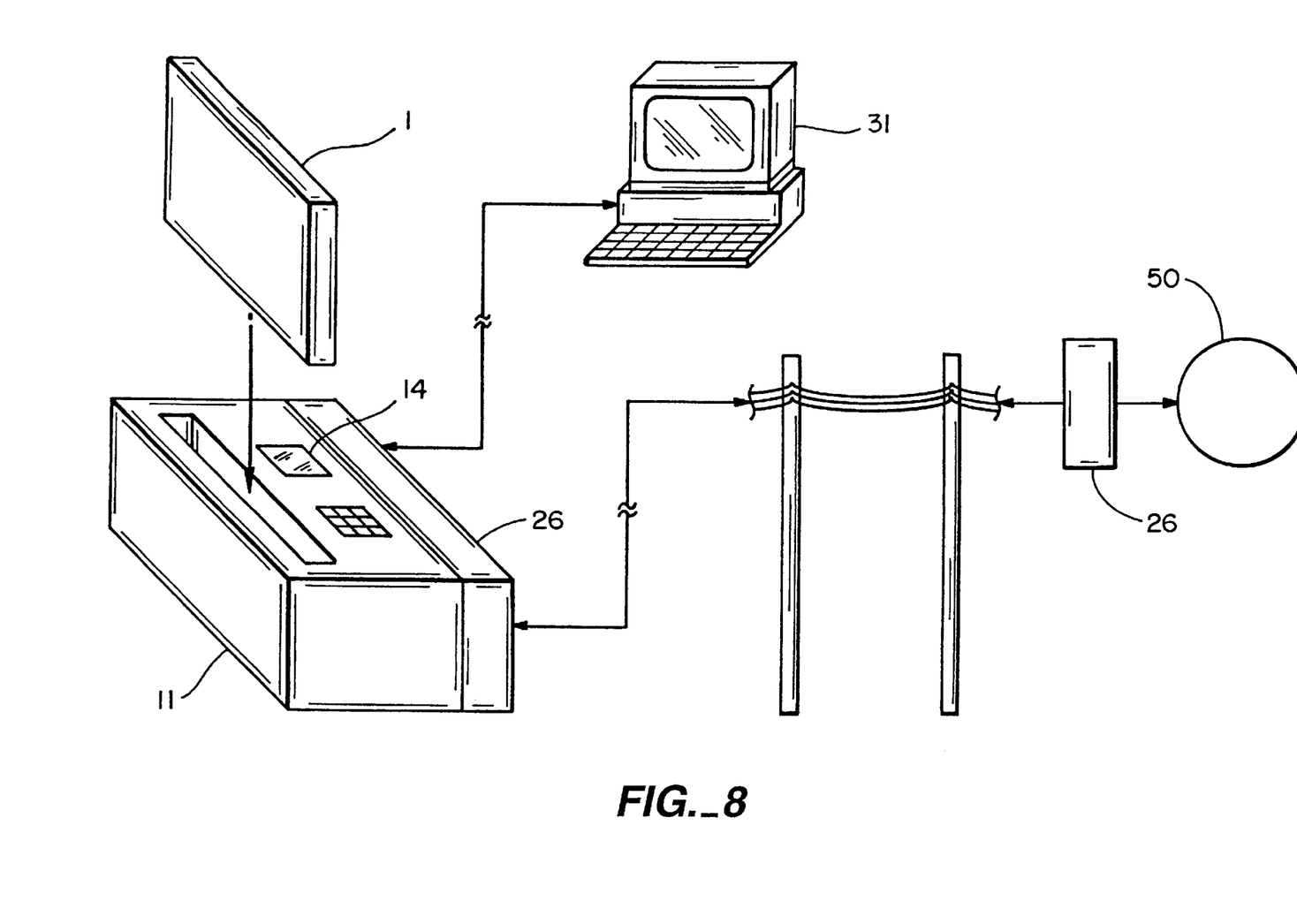
FIG. 8 is a schematic representation of the communication module in connection with the monitoring instrument and a remote location in accordance with a second embodiment of the invention.

Communication with the data storage system such as the remote site 50 or the computer 31 can be effected using a conventional modem operating in a known manner, as described above. However, modems are relatively expensive, and are complex in nature, relying on digital signal processing techniques to encode and transmit/receive information in analog form. As an alternative, a simpler, more cost-effective communication device 26, shown in FIG. 8, can be employed in order to reduce the cost of the overall system. This is accomplished by the implementation of a communication system designed specifically for using simple symbolic methods such a Morse code, DTMF (Dual-Tone Multifrequency) and Binary Coded Decimal techniques which is limited to the transfer of simple numbers and letters using a mneumonic system. By reducing the transmittable information to a relatively small set—typically comprising around ten characters—then the data can be transferred to and from device 26 using low speed transmission techniques. However, with the combination of a simple set of possible data variables and mneumonic transfer code a high rate of data transmission is achieved. Morse code, DTMF, Baudot, ASCII and Binary coded Decimal techniques can be seen as mneumonic short hand for the transmission of data because the data is condensed or reduced to a series of tones or pulses which always represent the same pieces of data. An example is DTMF which is a signaling method in which pairs of specific frequencies are used to indicate digits. DTMF uses the following eight frequencies to send or receive numeric data: 697 Hz, 770 Hz, 852 Hz, 941 Hz, 1209 Hz, 1336 Hz, 1477 Hz and 1633 Hz. Pairs of these frequencies are combined to encode a specific bit of information. For example, if the device 26 was sending a 1, the two out of seven code transmission would be 697 Hz and 1209 Hz. The two out of seven code DTMF matrix is shown below:

| Low Group Tones | High Group Tones | | |
| --- | --- | --- | --- |
| | 1209 Hz | 1336 Hz | 1477 Hz |
| 697 Hz | 1 | 2 | 3 |
| 770 Hz | 4 | 5 | 6 |
| 852 Hz | 7 | 8 | 9 |
| 941 Hz | * | 0 | # |

This code can be used to send information such as fixed or floating point data by using the "*" symbol as a decimal point and the "#" symbol as a delimiter. If additional tones are used even simple character data could be transmitted. For example, using a 1633 Hz column then "A" could be 697 Hz and 1633 Hz code and so forth. Thus using no more than eight discrete tones in this case, all transmittable information used in the operation in accordance with the invention can be encoded, and simple transmit and receive devices can be utilized in lieu of conventional modems such as modem 16. Such devices are well known and can be obtained at a fraction of the cost of conventional modems.

Alternatively, the device 26 could use Morse code to transmit similar information by using either analog pulses or frequency tones as the dots, dashes and spaces used in Morse code. Again a reduced set of discrete signals is used, rather than the complex analog modem alternative, and an attendant cost saving is realized. The analog pulses could be either dial pulse or frequency pulses. The system could also be configured with a DTMF tone to represent either the dot or dash. If 697 Hz was a dot, 852 Hz a dash, 1633 Hz a space then the code could be sent with a series of tones of specific duration. The use of a dial pulse could also be substituted and this in accomplished through a momentary interruption in the direct current in the loop of the calling system. Accordingly, the system can be limited to a set of three distinct characters used to encode the transmitted information, the characters comprising the dot, dash, and space as encoded in any desired manner, for example DTMF.

| Digit | Morse Code | DTMF |
|-------|------------|------|
| 1 | .---- | 697 Hz, 825 Hz, 852 Hz, 852 Hz, 852 Hz |
| 2 | ..--- | 697 Hz, 697 Hz, 852 Hz, 852 Hz, 852 Hz |
| 3 | ...-- | 697 Hz, 697 Hz, 697 Hz, 852 Hz, 852 Hz |
| 4 | ....- | 697 Hz, 697 Hz, 697 Hz, 697 Hz, 852 Hz |
| 5 | ..... | 697 Hz, 697 Hz, 697 Hz, 697 Hz, 697 Hz |
| 6 | -.... | 852 Hz, 852 Hz, 852 Hz, 852 Hz, 697 Hz |
| 7 | --... | 852 Hz, 852 Hz, 852 Hz, 697 Hz, 697 Hz |
| 8 | ---.. | 852 Hz, 852 Hz, 697 Hz, 697 Hz, 697 Hz |
| 9 | ----. | 852 Hz, 697 Hz, 697 Hz, 697 Hz, 697 Hz |
| 0 | ----- | 825 Hz, 825 Hz, 852 Hz, 852 Hz, 852 Hz |

Similar systems could be arranged with Baudot or ASCII systems. The idea could be modified so that the number of dial pules indicated the value to be sent separated by predetermined length of space as the delimiter between digits. An alternate method would be to assign a dot or dash value to a specific dial pulse signal such as 1dial pulse is a dot, 2 dial pulse is a dash and using two predetermine length of time between dial pulses as delimiters between dots & dashes and between digits. This would permit the system to send data at high speeds using the momentary interruption of the direct current of the phone system. If the data was all decimal information then each digit is represented by 5 dots or dashes and the separation indicator BT is represented by _..._, end of transmission is represented by ._._. and Wait is represented by ._.... . These could all be used as delimiters to achieve logical breaks between data and identify CRC data. The ASCII code requires a minimum of seven separate indicators to be sent for each digit but this could be truncated to 4 if only digits were being transmitted. The delimiters available using a 4 digit code could be colon, semi colon, less than, greater than, equal to, and question mark. The Baudot code requires 5 digits to be transmitted.

A typical session could be formed with the following sequence of steps. The communication device 26 dials the appropriate telephone address (number) and initiates the session. A CRC which indicated the check sum of the data would be sent followed by a delimiter. The data would then be transferred following a specific format of the data. Any of the transmission systems discussed (DTMF or digital pulse coupled with either Mores Code, Baudot, or ASCII for example) could be used to send the data. For a blood glucose monitoring device, one possible format is: blood glucose level-3 digits; month-2 digits; day-2 digits; hour-2 digits; minute-1 digit, in 6 minute segments. An example is 1201201091 which would equal 120 mg/dl on December 1 at 09:10. Various data could be compressed into this scheme and various applications could then have a reasonably priced data collection system. The complete session could be as follows:

| Sending device | Answering device |
|---|---|
| Dial the telephone address | |
| | Answer the call |
| | Send a start indicator/delimiter "#" |
| Send the CRC followed by a delimiter # | |
| Send the Social Security # and patient ID | |
| Send the blood glucose information 1201201091 | |
| Send the end of transmission delimiter # | |
| | Calculate the CRC and check |

This methodology reduces the cost of data collection in the following ways. The cost of the communication equipment is reduced due to the elimination of the more robust modem technology and its associated Digital Single Process (DSP) electronics at both ends of the transaction. A low cost device is designed to receive specific DTMF tones or dial pulses and feed them to a simple microprocessor for decoding the signal. The use of a digital pulse system is such that simple transistor switching systems can be used to receive the information. Additionally, by being able to send compact and specific information the connection time required to send the information is reduced, which reduces the cost of the transmission. Currently slow speed 300 to 9600 baud full function modems have a cost which starts at $20.00 for components alone. A dial pulse system of the current invention has a cost of $30.00. It is within the purview of the invention to use a system based on a 4 to 8 bit Microcontroller such as the Intel 8051 using FSK with data compression to increase the speed of the transfer. Various data compression techniques could be utilized to reduce the amount of data transferred in a known manner.

The invention does not require the patient to have any knowledge of computerized systems to complete the download and transfer features, making the data collection available to a large number of patients who do not have or use a computer system. The data is automatically exchanged in this case via modem to the remote data collection site along with information identifying the patient and/or the medical professional who monitors the patient. This permits medical professionals the ability to review their patients' disease management state at intervals other than during regular appointments by e.g. logging into the data collection site via the bulletin board or internet connection. This provides many advantages to patients by permitting them to have a storage location which can be used to monitor the long-term control of their disease.

The remote or local data storage system collects the information which is transferred from the monitoring instrument 1 and synchronizes and compiles it to eliminate duplicates from frequent uploads and interleafing of monitoring results if the patient is using more than one monitoring instrument 1 as is contemplated. The time and data recording associated with each result may be used to accomplish this function. The data storage system associated with the invention can be developed from either relational or table driven database technologies, including software using Oracle™, Informix™, and Microsoft Access™ engines. The system can also work with a discrete file system using a data management sub-system to effectively handle the numerous files.

A typical layout of the associated data to be stored in the data storage module of the invention includes time, date, monitoring reading, calories eaten, insulin dosage, and time after exercise. However, many different pieces of information could be captured by a monitoring instrument 1 and transferred to the data storage system at the remote location 50 by operation of the system of the invention. The invention is intended to permit the patient to capture his or her disease state condition and store it for review and therapy modification.

One advantage of the invention is the simplification of the data capture method and the presence of a data collection system which is accessible by all patients to capture their data and permit it to be reviewed by their specific health care professional. An additional benefit is the simplification of the disease management by elimination of the need for noncomputer-trained patients to manually record all their data. Another benefit of the system is the reduction in size and the convenience provided by elimination of the data communication functions and elimination or reduction in size of the user interface required to scroll through data stored in the monitoring instrument 1, set time and date, and communicate with current data management systems. Another advantage is that the communication module 11 can be used to recharge the batteries in the monitoring 1 system to reduce the size of the device by minimizing the battery size.

In accordance with the invention, the monitoring instrument is designed or selected to work with the communication module 11. However, the communication module 11 can alternately be designed to work with a number of monitoring instruments for increased versatility. Similarly, it is possible to eliminate the microprocessor 13 of communication module 11, along with random access memory 18 and use microprocessor 3 and memory module 4 of monitoring instrument 1. Additionally, the memory module 4 of the monitoring instrument can be designed to be removable such that it can interface, as a stand alone unit, with the communication module 11 to effect the information data exchange.

An advantage of the invention is the simplification of the data capture method and the presence of a data collection system which is accessible by all patients to capture their data and permits it to be reviewed by their specific health care professional. An additional benefit is the simplification of the disease management by elimination of the need for noncomputer-trained patients to manually record all their data. Another benefit of the system is the reduction in size and the convenience provided by elimination of the data communication functions and elimination or reduction in size of the user interface means required to scroll through data stored in the meter, set time and date, and communicate with current data management systems. Another advantage is that the communication module can be used to recharge the batteries in the monitoring system to reduce the size of the device by minimizing the battery size. The invention is intended to permit patients to capture their disease state condition and store them at local or remote locations for review and therapy modification.

The above are exemplary modes of carrying out the invention and are not intended to be limiting. It will be apparent to those skilled in the art that modifications thereto can be made without departure from the spirit and scope of the invention as set forth by the following claims.

What is claimed is:

1. A device for collecting and communicating analyte concentration information comprising:

a monitoring instrument adapted to operate in a collection mode and an interface mode in accordance with predetermined parameters, the monitoring instrument receiving the analyte concentration information and generating and storing information data representative of the analyte concentration information in the collection mode; and a communication module adapted to operate in the interface mode and a transmission mode, the communication module interfacing with the monitoring instrument to download the information data from the monitoring instrument in the interface mode, the communication module selectively transmitting the information data to an internet site and/or an electronic bulletin board in the transmission mode, the communication module comprising:

a communication port for effecting the interfacing of the communication module with the monitoring instrument;

a communication means for effecting the transmission of the information data to the internet site and/or electronic bulletin board, the communication means encoding the information data in a format selected from the group consisting of morse code, DTMF, Baudot, ASCII and Binary-Coded Decimal; and an input means capable of inputting at least a portion of the predetermined parameters to the communication module.

2. The device of claim 1, wherein the analyte concentration information is representative of the concentration of at least one blood analyte.

3. The device of claim 1, wherein the analyte concentration information is representative of blood glucose concentration.

4. The device of claim 1, wherein the analyte concentration information is representative of the concentration of at least one urine analyte.

5. The device of claim 1, wherein the analyte concentration information is representative of the concentration of at least one interstitial fluid analyte.

6. The device of claim 1, wherein the communication module comprises a display means for displaying the predetermined parameters and/or the information data.

7. The device of claim 6, wherein the input means is adapted to manipulate the displayed predetermined parameters and/or information data.

8. The device of claim 6, wherein one or both of the display means and the input means are adapted to compensate for vision impairment and/or hearing impairment.

9. The device of claim 1, further comprising a remote processing system adapted to manipulate the information data, the communication means comprising a data exchange module for effecting communication between the remote processing system and the communication module.

10. The device of claim 9, wherein the predetermined parameters are input to the communication module from the remote processing system.

11. The device of claim 10, wherein the predetermined parameters comprise date and time entries.

12. The device of claim 11, wherein the remote processing system is adapted to synchronize and interleaf the information data according to the date and time entries and to sort the information data according to patient and/or medical professional identification information.

13. The device of claim 1, wherein the input means is a voice recognition system.

14. The device of claim 1, wherein the communication means comprises a modem.

15. The device of claim 14, wherein the remote location is an internet site accessed through the modem.

16. The device of claim 15, wherein the information data includes representations of one or more of monitoring readings, time and date stamps, meal times, exercise times, and therapy amounts.

17. The device of claim 1, wherein the predetermined parameters are input to the communication module from the internet site and/or electronic bulletin board.

18. The device of claim 17, wherein the predetermined parameters comprise time and date entries.

19. The device of claim 18, wherein the internet site and/or electronic bulletin board is adapted to synchronize and interleaf the information data according to the date and time entires and to sort the information data according to patient and/or medical professional identification information.

20. The device of claim 18, wherein the information data includes one or more of monitoring readings, time and date stamps, meal times, exercise times, and therapy amounts.

21. The device of claim 1, wherein the monitoring instrument operates as a stand alone unit independent of the communication module in the collection mode and is adapted to effect multiple collection mode operations prior to operation in the interface mode.

22. The device of claim 1, wherein the monitoring instrument further comprises a rechargeable battery for powering the monitoring instrument, and wherein the communication module further comprises a battery recharger for charging the rechargeable battery in the interface mode.

23. The device of claim 1, wherein the internet site and/or electronic bulletin board is adapted to be selected through the input means.

24. The device of claim 1, further comprising a processor for controlling the operation of the communication module.

25. The device of claim 24, wherein the processor is disposed in the monitoring instrument.

26. The device of claim 1, wherein the communication port is a first engaging portion disposed in the communication module and adapted to mate with a second engaging portion disposed on the monitoring instrument.

27. The device of claim 26, wherein the mating activates the interface mode.

28. The device of claim 26, wherein the mating activates the transmission mode.

29. The device of claim 1, wherein the communication port is a cable which plugs into the monitoring instrument and the communication module.

30. The device of claim 1, wherein the information data includes representations of one or more of monitoring readings, time and date stamps, meal times, exercise times, and therapy amounts.

31. The device of claim 1, wherein the monitoring instrument is provided with a removable memory module, the memory module storing the information data in the collection mode, and interfacing with the communication module, as a stand-alone unit, in the interface mode.

32. The device of claim 1, wherein the communication module encodes the information data using a set of no more than ten characters.

33. The device of claim 1, wherein the communication module encodes the information data using a set of no more than eight characters.

34. A communication device for manipulating information data representative of analyte concentration information, the communication device comprising:
  means for generating the analyte concentration information;
  means for conveying the analyte concentration information into digital form;
  means for encoding the information data in a format selected from the group consisting of morse code, DTMF, Baudot, ASCII, and Binary-Coded Decimal
  means for transmitting the converted analyte concentration information to an internet site and/or an electronic bulletin board.

35. The device of claim 34, wherein the means for converting encodes the analyte concentration information using a set of no more than ten characters.

36. The device of claim 34, wherein the means for converting encodes the analyte concentration information using a set of no more than eight characters.

37. A method for collecting and communicating analyte concentration information comprising:
  gathering, in a collection mode, the analyte concentration information in an monitoring instrument;
  generating, in the collection mode, information data representative of the analyte concentration information;
  downloading, in an interfacing mode, the information data from the monitoring instrument to a communication module;
  encoding the information data in a format selected from the group consisting of morse code, DTMF, Baudot, ASCII and Binary-Coded Decimal; and
  selectively sending the encoded information data, in a transmission mode, from the communication module to at least one of an internet site and an electronic bulletin board.

38. The method of claim 37, wherein the analyte concentration information is representative of the concentration of at least one blood analyte.

39. The method of claim 37, wherein the analyte concentration information is representative of blood glucose concentration.

40. The method of claim 37, wherein the analyte concentration information is representative of the concentration of at least one urine analyte.

41. The device of claim 37, wherein the analyte concentration information is representative of the concentration of at least on interstitial fluid analyte.

42. The method of claim 37, wherein the communication module is provided with a display means for displaying the information data.

43. The method of claim 37, further comprising the step of manipulating the information data using a remote processing system.

44. The method of claim 37, wherein at least one of the collection, interfacing and transmission modes is governed by predetermined parameters communicated to the communication module from a remote location.

45. The method of claim 37, wherein the predetermined parameters comprise date and time entries.

46. The method of claim 37, wherein the information data includes one or more of monitoring readings, time and date stamps, meal times, exercise times, and therapy amounts.

47. The method of claim 37, wherein the monitoring instrument operates as a stand alone unit independent of the communication module in the collection mode and is adapted to effect multiple collection mode operations prior to operation in the interface mode.

48. The method of claim 37, wherein the monitoring instrument is provided with a rechargable battery for powering the monitoring instrument, and wherein the communication module is provided with a battery recharger for charging the rechargable battery in the interface mode.

49. The method of claim 37, wherein the step of selectively sending comprises using an input means to select one of the internet site or electronic bulletin board.

50. The method of claim 37, further comprising the step of using a processor for controlling the operation of the communication module.

51. The method of claim 37, wherein the processor is disposed in the monitoring instrument.

52. The method of claim 42, wherein the display means is adapted to compensate for vision impairment.

53. The method of claim 37, wherein the communication module is responsive to voice commands.

54. The method of claim 42, wherein the display means is adapted to compensate for hearing impairment.

55. The method of claim 43, wherein at least one of the collection, interfacing and transmission modes is governed by predetermined parameters communicated to the communication means from the remote processing system, the predetermined parameters comprising date and time entries, and wherein the remote processing system is adapted to synchronize and interleaf the information data according to the date and time entries.

56. The method of claim 37, wherein the interfacing mode is effected using a communication port.

57. The method of claim 56, wherein the communication port is a cable adapted to plug into the monitoring instrument and the communication module.

58. The method of claim 56, wherein the communication port is a first engaging portion disposed in the communication module and adapted to mate with a second engaging portion disposed on the monitoring instrument.

59. The method of claim 58, wherein the mating activates the interface mode.

60. The method of claim 58, wherein the mating activates the transmission mode.

61. The method of claim 37, further comprising the step of encoding the information data using a set of no more than ten characters.

62. The method of claim 37, further comprising the step of encoding the information data using a set of no more than eight characters.

63. A method of manipulating information data representative of analyte concentration information, the method comprising the steps of:

generating the analyte concentration information;

converting the analyte concentration information into digital form; and encoding the converted analyte concentration information in a format selected from the group consisting of morse code, DTMF, Baudot, ASCII, and Binary-Coded Decimal; and transmitting the encoded analyte concentration information to a remote location.

64. The method of claim 63, wherein the step of converting comprises encoding the analyte concentration information using a set of no more than ten characters.

65. The method of claim 63, wherein the step of converting comprises encoding the analyte concentration information using a set of no more than eight characters.

\* \* \* \* \*